United States Patent
Okabe et al.

(10) Patent No.: US 10,456,072 B2
(45) Date of Patent: Oct. 29, 2019

(54) IMAGE INTERPRETATION SUPPORT APPARATUS AND METHOD

(71) Applicant: FUJIFILM Corporation, Tokyo (JP)

(72) Inventors: Yuuki Okabe, Tokyo (JP); Mayuko Ikuta, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 86 days.

(21) Appl. No.: 15/891,556

(22) Filed: Feb. 8, 2018

(65) Prior Publication Data

US 2018/0177446 A1    Jun. 28, 2018

Related U.S. Application Data

(63) Continuation of application No. PCT/JP2016/065559, filed on May 26, 2016.

(30) Foreign Application Priority Data

Aug. 24, 2015 (JP) .................................. 2015-164601

(51) Int. Cl.
G06K 9/00 (2006.01)
A61B 5/16 (2006.01)
(Continued)

(52) U.S. Cl.
CPC .............. *A61B 5/163* (2017.08); *A61B 3/113* (2013.01); *A61B 5/1103* (2013.01); *A61B 5/746* (2013.01);
(Continued)

(58) Field of Classification Search
None
See application file for complete search history.

(56) References Cited

U.S. PATENT DOCUMENTS

| 8,020,993 B1 * | 9/2011 | Fram ....................... G06F 3/013 351/200 |
| 8,696,121 B1 * | 4/2014 | Fram ....................... G06F 3/013 351/200 |

(Continued)

FOREIGN PATENT DOCUMENTS

| JP | H03-070381 A | 3/1991 |
| JP | 2000-342537 A | 12/2000 |

(Continued)

OTHER PUBLICATIONS

International Search Report; issued in PCT/JP2016/065559; dated Aug. 23, 2016.

(Continued)

*Primary Examiner* — Soo Jin Park
(74) *Attorney, Agent, or Firm* — Studebaker & Brackett PC

(57) ABSTRACT

An image interpretation support apparatus includes a line-of-sight detecting unit that detects a line of sight of a person who reads the image, a gaze determining unit that determines, in accordance with a detection result obtained by the line-of-sight detecting unit, whether a candidate lesion portion in an image to be interpreted that is displayed on a display unit has been gazed at by the person who reads the image, a completion detecting unit that detects completion of image interpretation, by the person who reads the image, of the image to be interpreted that is displayed on the display unit, and a display control unit that, in a case where the completion detecting unit detects the completion of the image interpretation and the gaze determining unit determines that the candidate lesion portion has not been gazed at, switches from a first display state to a second display state.

20 Claims, 15 Drawing Sheets

(51) Int. Cl.
*A61B 3/113* (2006.01)
*A61B 5/11* (2006.01)
*A61B 5/00* (2006.01)
*A61B 6/00* (2006.01)

(52) U.S. Cl.
CPC .......... *A61B 6/461* (2013.01); *G06K 9/00335*
(2013.01); *A61B 6/5217* (2013.01); *G06K 9/00604* (2013.01)

(56) References Cited

U.S. PATENT DOCUMENTS

| | | | |
|---|---|---|---|
| 9,841,811 B2* | 12/2017 | Reiner | A61B 3/113 |
| 2007/0239005 A1 | 10/2007 | Ogasawara | |
| 2011/0206283 A1 | 8/2011 | Quarfordt et al. | |
| 2011/0270123 A1 | 11/2011 | Reiner | |
| 2015/0213725 A1* | 7/2015 | Huntley | A61B 5/168 345/156 |

FOREIGN PATENT DOCUMENTS

| | | |
|---|---|---|
| JP | 2005-348936 A | 12/2005 |
| JP | 2007-195892 A | 8/2007 |
| JP | 2007-319327 A | 12/2007 |
| JP | 2008-099929 A | 5/2008 |
| JP | 2009-125154 A | 6/2009 |
| JP | 2010-035756 A | 2/2010 |
| JP | 2011-175620 A | 9/2011 |
| JP | 2012-196279 A | 10/2012 |
| JP | 2014-123179 A | 7/2014 |
| JP | 2015-093147 A | 5/2015 |
| JP | 2015-097127 A | 5/2015 |

OTHER PUBLICATIONS

Written Opinion; issued in PCT/JP2016/065559; dated Aug. 23, 2016.

International Preliminary Report on Patentability; issued in PCT/JP2016/065559; dated Feb. 27, 2018.

The extended European search report issued by the European Patent Office dated Aug. 24, 2018, which corresponds to European Patent Application No. 16838863.5-1124 and is related to U.S. Appl. No. 15/891,556.

* cited by examiner

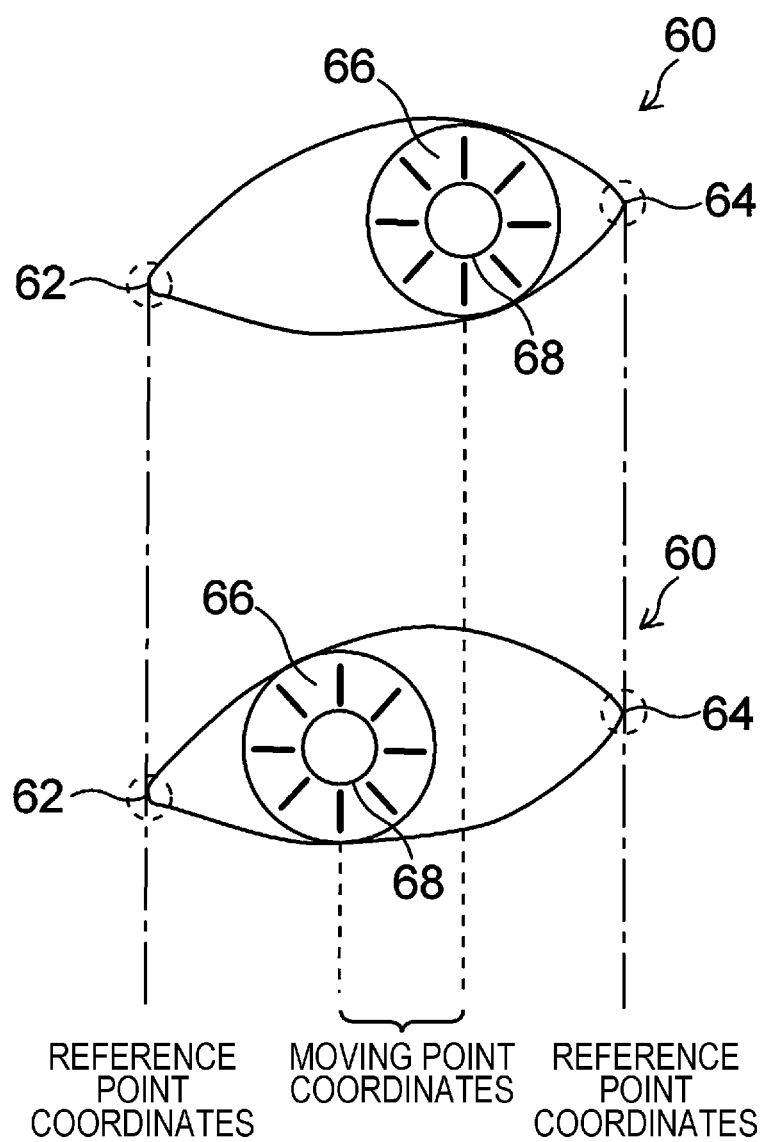

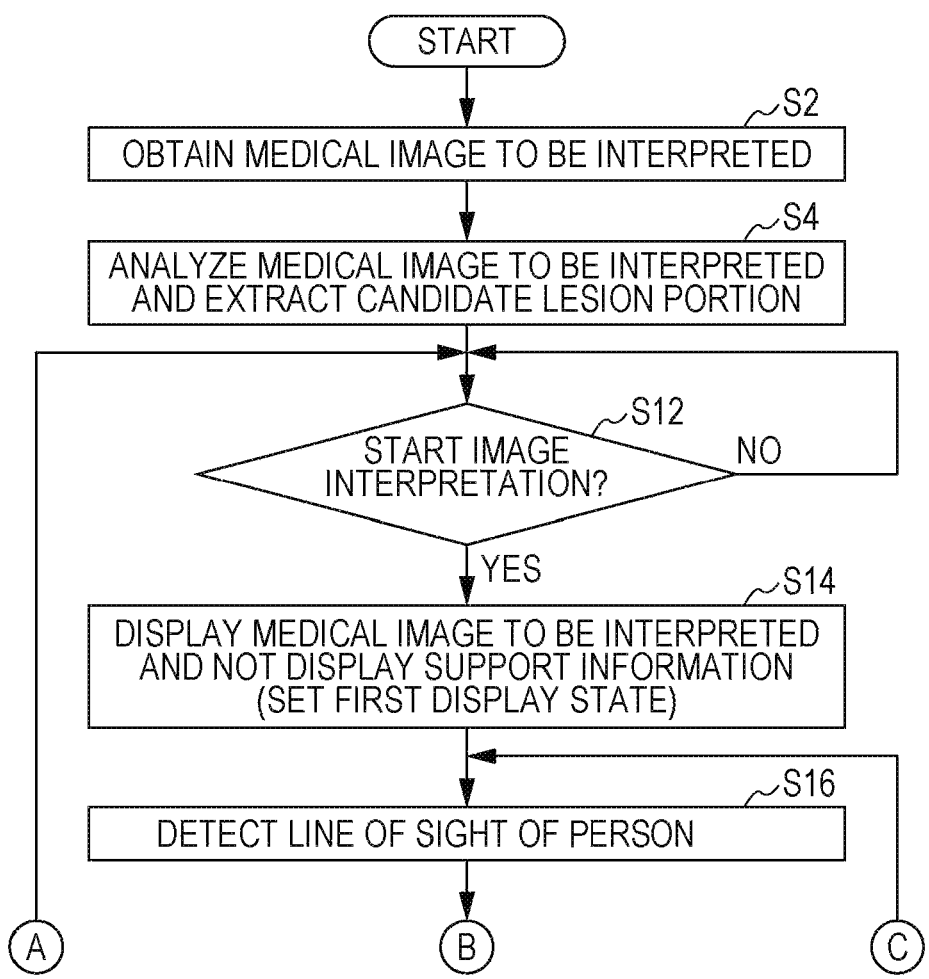

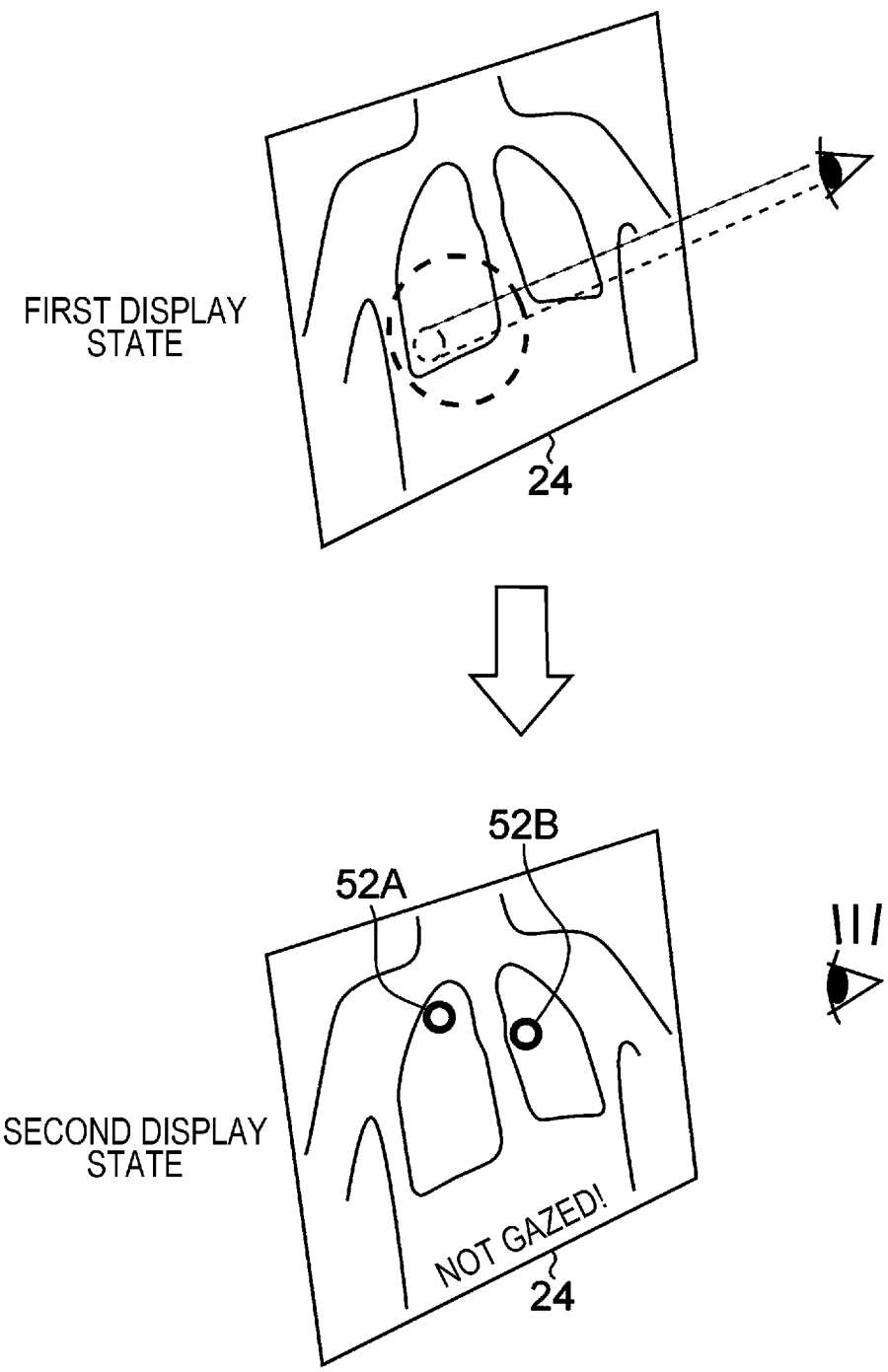

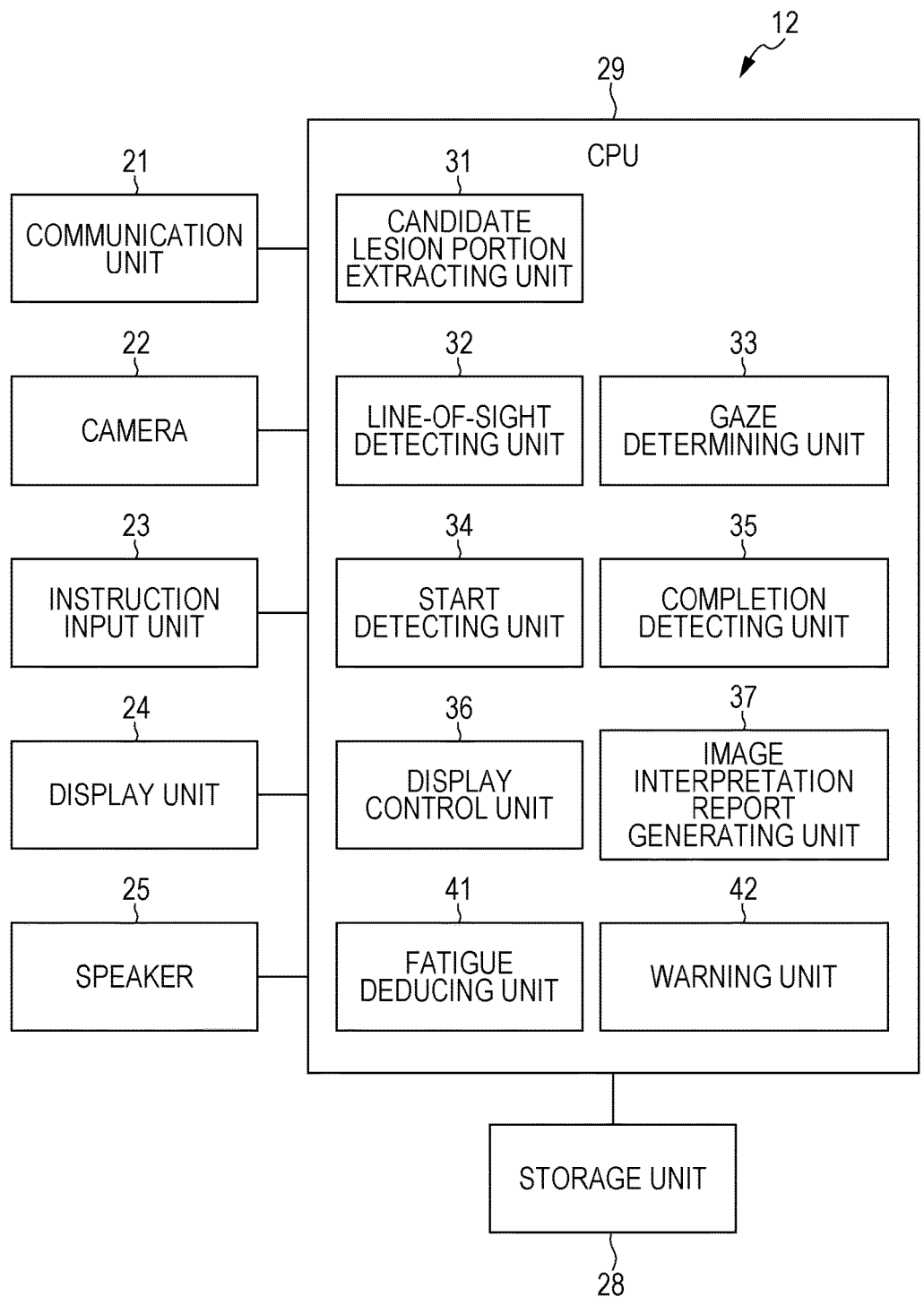

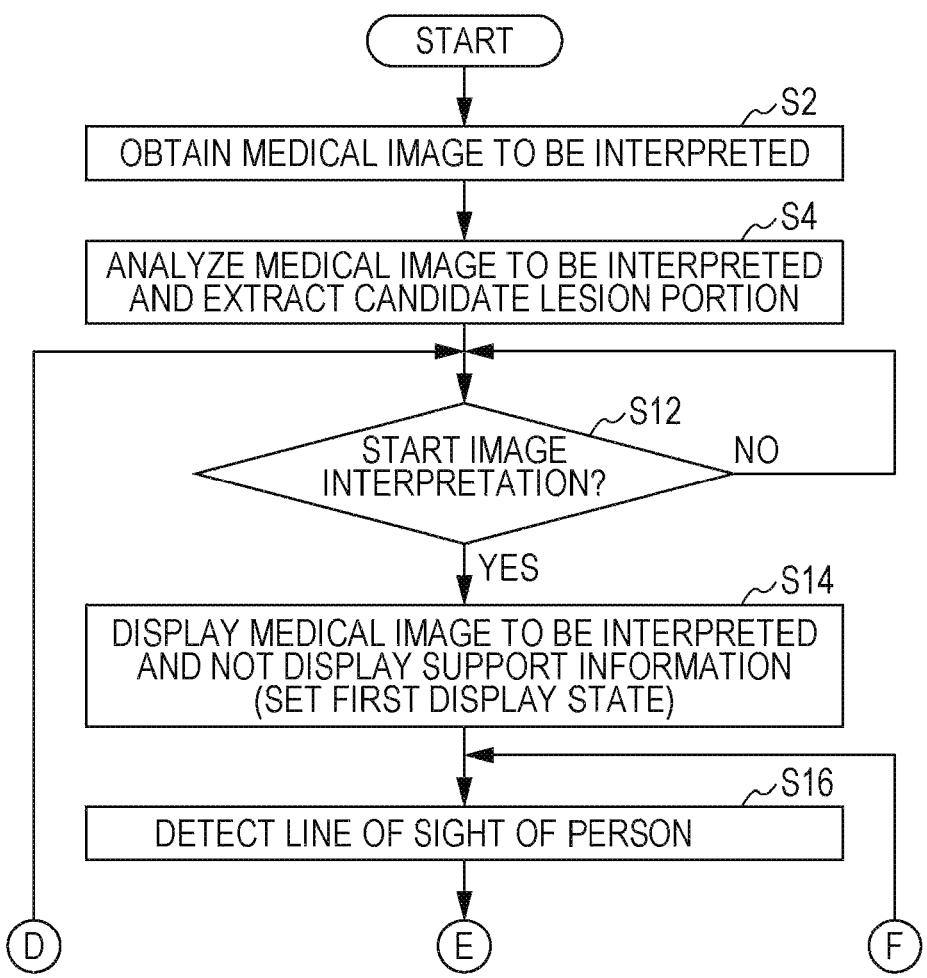

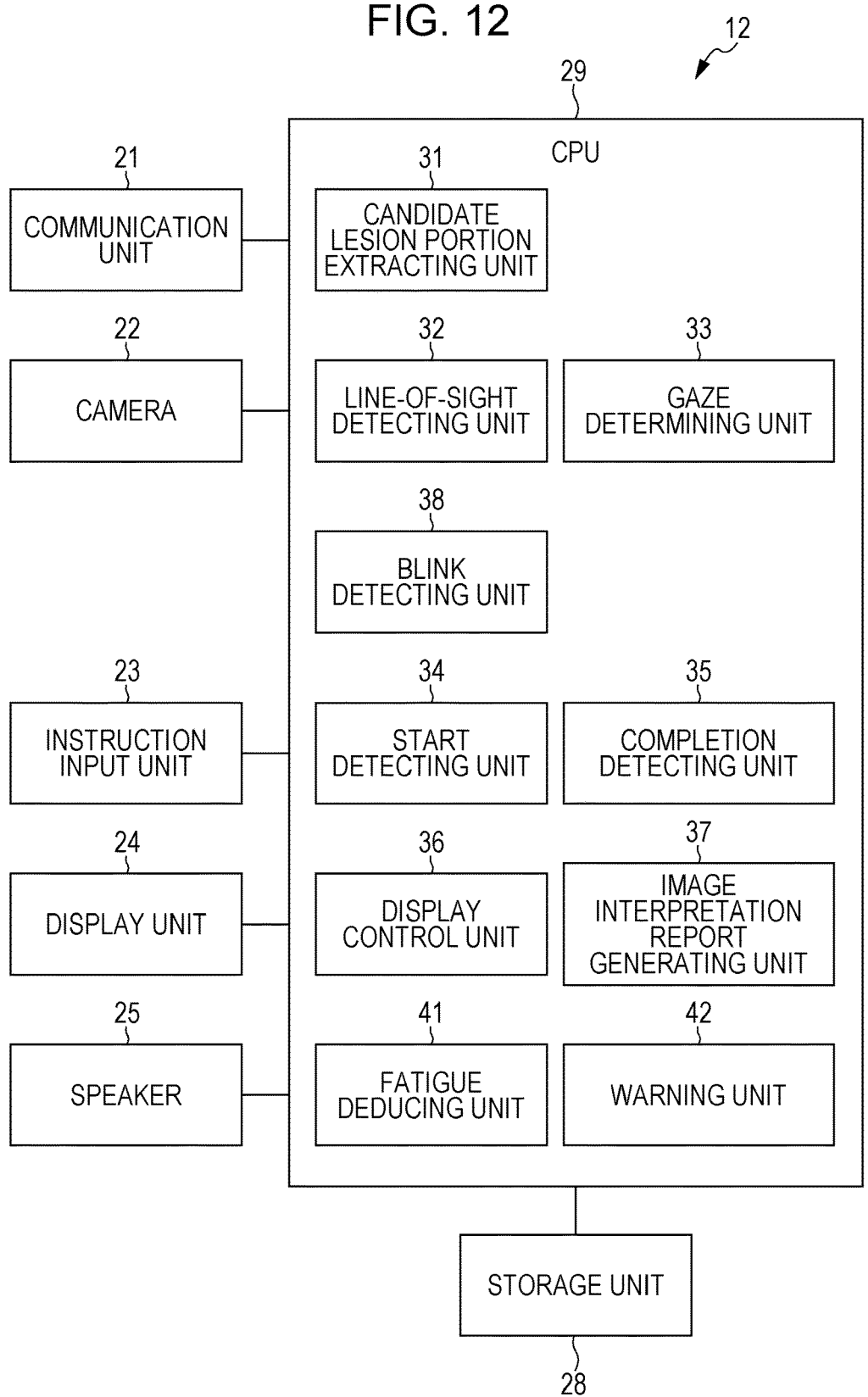

IMAGE INTERPRETATION SUPPORT APPARATUS AND METHOD

CROSS-REFERENCE TO RELATED APPLICATIONS

This application is a Continuation of PCT International Application No. PCT/JP2016/065559 filed on May 26, 2016, which claims priority under 35 U.S.C § 119(a) to Japanese Patent Application No. 2015-164601 filed on Aug. 24, 2015. Each of the above application(s) is hereby expressly incorporated by reference, in its entirety, into the present application.

BACKGROUND OF THE INVENTION

1. Field of the Invention

The present invention relates to an image interpretation support apparatus and method, and more specifically to an image interpretation support technique that does not interfere with image interpretation by a person who reads an image and enables the person who reads an image to avoid oversight.

2. Description of the Related Art

A person who reads an image sometimes interprets a large number of medical images (for example, X-ray images) in a day. Recently, there has been a shortage of experienced persons who read an image, leading to a trend towards an increased load on persons who read an image. In particular, medical doctors conducting periodical medical check-up and specializing in remote image interpretation are requested to interpret images in a short period of time, and they are at an increased risk of overlooking a lesion portion as a result. There is known a technique to avoid such oversight of a lesion portion, in which a candidate lesion portion, such as a shadow image present in a medical image to be interpreted, is automatically recognized by image processing, a mark (support information) to indicate the candidate lesion portion is displayed in the medical image, and consequently a person who reads an image is informed on which part of the medical image to be interpreted to gaze at during image interpretation (JP2015-97127A).

In addition, there is proposed medical equipment that enables a practitioner to input an instruction by voice, line of sight, or gesturing without touching anything in a situation of clinical practice where both hands of the practitioner are occupied (JP2015-93147A and JP2007-195892A).

SUMMARY OF THE INVENTION

However, for a person who reads an image to avoid oversight without interference during image interpretation performed by the person who reads an image is difficult.

This difficulty is caused by the following issues. If support information indicating a candidate lesion portion is displayed in a medical image by using the technique described in JP2015-97127A, the person who reads an image unintentionally relies on the support information too much, and autonomous interpretation by the person who reads an image is suppressed, or a lesion portion is visually obstructed by the support information, thereby interfering with image interpretation by the person who reads an image. To solve these issues, a method of displaying support information in a region that does not overlap a candidate lesion portion or a method of enabling switching between showing and hiding of support information in accordance with a decision by a medical doctor is considered. But these methods cause new issues such as a small image display region and a burden of a switching operation. Thus, it is difficult to consider these methods as an effective way to address an issue of avoiding oversight by the person who reads an image without interfering with image interpretation performed by the person who reads an image in the case where reliable image interpretation in a short period of time is requested.

The technique described in JP2015-93147A employs a configuration in which image operation such as enlargement and reduction is performed by using a combination of voice input and line-of-sight input, but reliable operation is hindered in an environment that is disturbed by noise, such as other human voices, background music, or the like because voice input is necessary. Even though an instruction can be input without touching anything, a burden of inputting instruction is still unavoidable.

The technique described in JP2007-195892A employs a configuration in which a command corresponding to a displayed icon is performed when a line-of-sight position is moved to the displayed icon and the displayed icon is gazed at for a predetermined period of time thereafter. However, an effect of avoiding interfering with image interpretation performed by a person who reads an image is not expected in this configuration because it is needed to move a line-of-sight position to the icon. Further, it is not possible to expect an effect in which a person who reads an image is able to avoid oversight.

In view of the foregoing issues, an object of the present invention is to provide an image interpretation support apparatus and method that do not interfere with image interpretation by a person who reads an image and enables the person who reads an image to avoid oversight.

To achieve the aforementioned object, an image interpretation support apparatus according to an aspect of the present invention includes a candidate lesion portion extracting unit that analyzes an image to be interpreted and extracts a candidate lesion portion from the image to be interpreted, a display unit that is capable of displaying the image to be interpreted and support information indicating the candidate lesion portion, a line-of-sight detecting unit that detects a line of sight of a person who reads the image, a gaze determining unit that determines, in accordance with a detection result obtained by the line-of-sight detecting unit, whether the candidate lesion portion in the image to be interpreted that is displayed on the display unit has been gazed at by the person who reads the image, a completion detecting unit that detects completion of image interpretation, by the person who reads the image, of the image to be interpreted that is displayed on the display unit, and a display control unit that, in a case where the completion detecting unit detects the completion of image interpretation and the gaze determining unit determines that the candidate lesion portion has not been gazed at, switches from a first display state in which the image to be interpreted is displayed on the display unit and the support information is not displayed to a second display state in which at least the support information is displayed on the display unit.

The display control unit may keep the first display state in a case where the completion detecting unit detects the completion of image interpretation and the gaze determining unit determines that the candidate lesion portion has been gazed at.

In a case where the completion detecting unit detects completion of image interpretation and the gaze determining unit determines that the candidate lesion portion has been gazed at, the display control unit may switch the display unit to a display state in which the support information is not displayed and that is different from the first display state.

The phrase "detects completion of image interpretation" of this aspect means not only a case of detecting input of an instruction (such as manual operation, voice input, gesturing, or the like), provided by the person who reads the image, to indicate completion of image interpretation, but also a case of detecting or deducing the intention of the person who reads the image to complete image interpretation without explicit input of an instruction, provided by the person who reads the image, to indicate completion of image interpretation (for example, a case of detecting or deducing by analyzing, through image processing, a person image obtained by capturing an image of the person who reads the image).

According to this aspect, in a case where the completion detecting unit detects completion of image interpretation and the gaze determining unit determines that the candidate lesion portion has been gazed at, the support information remains hidden. On the other hand, in a case where the completion detecting unit detects completion of image interpretation and the gaze determining unit determines that a candidate lesion portion has not been gazed at, the support information to indicate the candidate lesion portion is displayed for the person who reads the image. Accordingly, the person who reads the image can gaze at the lesion portion with a high degree of concentration without the interference of the support information during the image interpretation. In addition, if a candidate lesion portion that has not been gazed at is present in a case where the image interpretation is completed, the person who reads the image is notified of the fact and resumes image interpretation. In short, according to this aspect, the person who reads the image can avoid oversight without the interference during image interpretation.

In an image interpretation support apparatus according to another aspect of the present invention, in a case where a plurality of candidate lesion portions are present in the image to be interpreted, in the second display state, the display control unit performs control not to display support information for a candidate lesion portion that the person who reads the image has gazed at among the plurality of candidate lesion portions, and the display control unit performs control to display support information for a candidate lesion portion that the person who reads the image has not gazed at. According to this aspect, the person who reads the image can gaze, with a high degree of concentration, at only a candidate lesion portion that has not been gazed at among the plurality of candidate lesion portions, and accordingly efficiency of image interpretation improves.

In an image interpretation support apparatus according to another aspect of the present invention, in a case where a plurality of candidate lesion portions are present in the image to be interpreted, the display control unit performs control to display, in a changed display mode, a candidate lesion portion that the person who reads the image has gazed at among the plurality of candidate lesion portions so as to discriminate the candidate lesion portion that the person who reads the image has gazed at from a candidate lesion portion that the person who reads the image has not gazed at. According to this aspect, the person who reads the image can gaze, with a high degree of concentration, at only a candidate lesion portion that has not been gazed at, for which the display mode is unchanged, because the candidate lesion portion that has been gazed at, for which the display mode is changed as the line of sight of the person who reads the image moves, is removed. In short, performing display control by interactively responding to movement of the line of sight of the person who reads the image enables the efficiency of image interpretation to improve.

An image interpretation support apparatus according to another aspect of the present invention includes a fatigue deducing unit that deduces whether the person who reads the image needs recovery from fatigue caused by the image interpretation, and a warning unit that outputs a warning in a case where the fatigue deducing unit deduces that the recovery from fatigue is needed. According to this aspect, in a case where the person who reads the image is tired, the person who reads the image is advised to take a rest. In short, the person who reads the image can keep concentrating.

In an image interpretation support apparatus according to another aspect of the present invention, the fatigue deducing unit deduces whether the recovery from fatigue is needed by using the number of switching operations from the first display state to the second display state, performed by the display control unit.

In an image interpretation support apparatus according to another aspect of the present invention, the fatigue deducing unit deduces whether the recovery from fatigue is needed by using an accumulated duration of the image interpretation.

In an image interpretation support apparatus according to another aspect of the present invention, the fatigue deducing unit deduces whether the recovery from fatigue is needed by using at least one of a moving speed or an amount of movement of the line of sight that is detected by the line-of-sight detecting unit.

An image interpretation support apparatus according to another aspect of the present invention includes a blink detecting unit that detects a blink of eyes of the person who reads the image, wherein the fatigue deducing unit deduces whether the recovery from fatigue is needed by using a speed of the blink of the eyes. According to this aspect, the possibility that an individual characteristic leads to an incorrect conclusion that the person who reads the image, who is not tired, is tired is reduced. In short, it is possible to reduce the frequency of outputting warnings due to incorrect conclusions.

In an image interpretation support apparatus according to another aspect of the present invention, the fatigue deducing unit deduces whether the recovery from fatigue is needed in accordance with individual data of the person who reads the image.

In an image interpretation support apparatus according to another aspect of the present invention, the display control unit performs control to display an enlarged image of a region at which the line of sight is directed in the image to be interpreted, and stops performing control to display the enlarged image of the region, in a case where the line of sight moves away from the region or when a fixed period of time has elapsed from when the display control unit starts performing control to display the enlarged image of the region.

In an image interpretation support apparatus according to another aspect of the present invention, the display control unit decreases visibility of a portion that does not need to be gazed at in the image to be interpreted compared with visibility of the candidate lesion portion.

In an image interpretation support apparatus according to another aspect of the present invention, input of an instruction from the person who reads the image is received in accordance with a line-of-sight detection performed by the line-of-sight detecting unit.

In an image interpretation support apparatus according to another aspect of the present invention, in a case where the line of sight of the person who reads the image is directed at a candidate lesion portion in the image to be interpreted that is displayed on the display unit, the gaze determining unit determines whether the person who reads the image is in a gazing state in which the person who reads the image is gazing at the candidate lesion portion or in a non-gazing state in which the person who reads the image is not gazing at the candidate lesion portion while the line of sight of the person who reads the image is directed at the candidate lesion portion.

In an image interpretation support apparatus according to another aspect of the present invention, the gaze determining unit determines whether the person who reads the image is in the gazing state or in the non-gazing state by using a time during which the line of sight of the person who reads the image dwells on the candidate lesion portion.

In an image interpretation support apparatus according to another aspect of the present invention, the gaze determining unit determines whether the person who reads the image is in the gazing state or in the non-gazing state in accordance with a condition of a pupil of the person who reads the image.

An image interpretation support apparatus according to another aspect of the present invention includes a characteristic measuring unit that measures gaze characteristic of the person who reads the image for each individual and a criterion determining unit that determines a criterion for determining whether the person who reads the image is in the gazing state or in the non-gazing state for each individual by using a measurement result for each individual obtained by the characteristic measuring unit, and the gaze determining unit determines whether the person who reads the image is in the gazing state or in the non-gazing state in accordance with the criterion determined for each individual by the criterion determining unit.

In an image interpretation support apparatus according to another aspect of the present invention, the characteristic measuring unit displays a test pattern on the display unit, moves the test pattern on a screen of the display unit, and measures a tracking ability of the line of sight of the person who reads the image to the movement of the test pattern, and the gaze determining unit determines a criterion for determining whether the person who reads the image is in the gazing state or in the non-gazing state by using the tracking ability of the line of sight of the person who reads the image measured by the characteristic measuring unit.

An image interpretation support apparatus according to an aspect of the present invention includes an image interpretation deducing unit that deduces whether the person who reads the image has performed image interpretation in accordance with an enlarging operation performed on the image to be interpreted, and the completion detecting unit detects completion of image interpretation only in a case where the image interpretation deducing unit deduces that image interpretation has been performed.

An image interpretation support method according to an aspect of the present invention includes a step of analyzing an image to be interpreted and extracting a candidate lesion portion from the image to be interpreted, a step of setting a first display state in which the image to be interpreted is displayed on a display unit and support information that indicates the candidate lesion portion is not displayed, a step of detecting a line of sight of a person who reads the image, a step of determining whether the candidate lesion portion in the image to be interpreted that is displayed on the display unit has been gazed at by the person who reads the image in accordance with a result of detection of the line of sight, a step of detecting completion of image interpretation, by the person who reads the image, of the image to be interpreted that is displayed on the display unit, and a step of switching from the first display state in which the image to be interpreted is displayed on the display unit and the support information is not displayed to a second display state in which at least the support information is displayed on the display unit in a case where the completion of image interpretation is detected and gazing at the candidate lesion portion is not determined.

According to the present invention, avoiding oversight by a person who reads an image without interfering image interpretation performed by the person who reads the image is possible.

BRIEF DESCRIPTION OF THE DRAWINGS

FIG. 5 is an explanatory illustration used to describe an example of line-of-sight detection;

FIGS. 6A and 6B depict a flowchart illustrating a process flow of an example of an image interpretation support method using the image interpretation support apparatus of the first embodiment;

FIG. 7 is an explanatory illustration used to describe a transition from a first display state, in which a medical image to be interpreted is displayed and support information is not displayed, to a second display state, in which support information is displayed;

FIG. 10 is a block diagram illustrating a configuration example of an image interpretation support apparatus of a second embodiment;

FIGS. 11A and 11B depict a flowchart illustrating a process flow of an example of an image interpretation support method using the image interpretation support apparatus of the second embodiment;

FIG. 12 is a block diagram illustrating another configuration example of an image interpretation support apparatus of a second embodiment;

DESCRIPTION OF THE PREFERRED EMBODIMENTS

Hereinafter, embodiments of an image interpretation support apparatus and an image interpretation support method according to the present invention will be described with reference to the attached drawings.

Example of System Configuration

Figure 1:
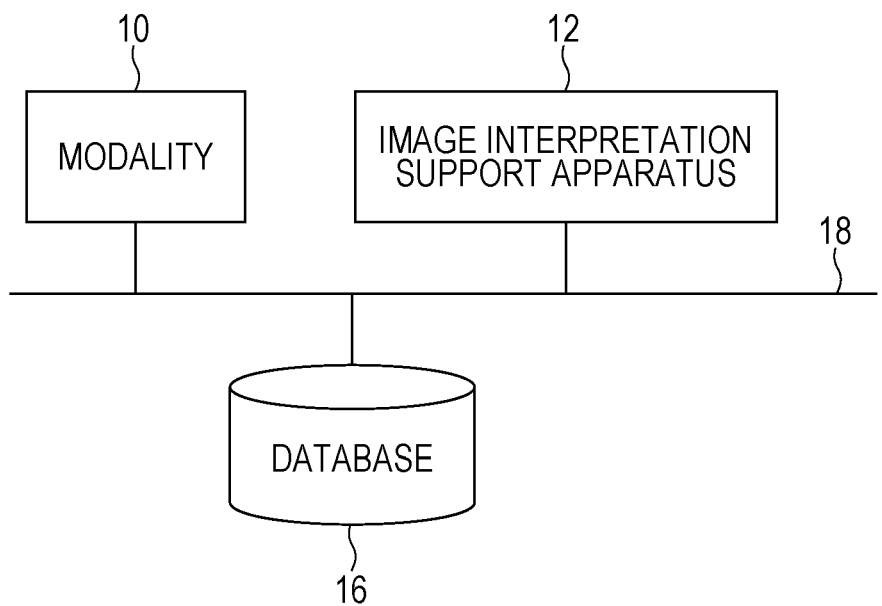
FIG. 1 is a system configuration diagram illustrating an example of a medical system including an image interpretation support apparatus according to an aspect of the present invention.

FIG. 1 is a system configuration diagram illustrating an example of a medical system including an image interpretation support apparatus according to an aspect of the present invention.

A medical system illustrated in FIG. 1 is constituted by a modality 10, an image interpretation support apparatus 12, and a database 16, which are connected to each other so as to be able to communicate with each other via a local area network 18.

Although FIG. 1 illustrates a configuration in which one apparatus of each kind is connected to the local area network 18 for the sake of description, a plurality of modalities of various types are connected to the local area network 18. In addition, a plurality of image interpretation support apparatuses 12, the number of which depends on the number of persons who reads images, are connected. A plurality of databases 16 may also be connected as distributed databases.

The modality 10 is a medical imaging apparatus that generates and outputs medical image data by imaging subjects (humans, animals, and the like). The modality 10 of this example adds additional information defined by the Digital Imaging and Communications in Medicine (DICOM) standard to the medical image data. Examples of the modality 10 include an X-ray imaging apparatus, a computed tomography (CT) imaging apparatus, a magnetic resonance imaging (MM) apparatus, a positron emission tomography (PET) imaging apparatus, an ultrasonography apparatus, and the like.

The image interpretation support apparatus 12 is an apparatus to support medical image interpretation performed by a person who reads an image. The image interpretation support apparatus 12 is implemented as, for example, a computer device. Specific examples will be described below.

The database 16 stores medical image data and data to support interpretation of medical images (support information data and the like described below).

First Embodiment

Figure 2:
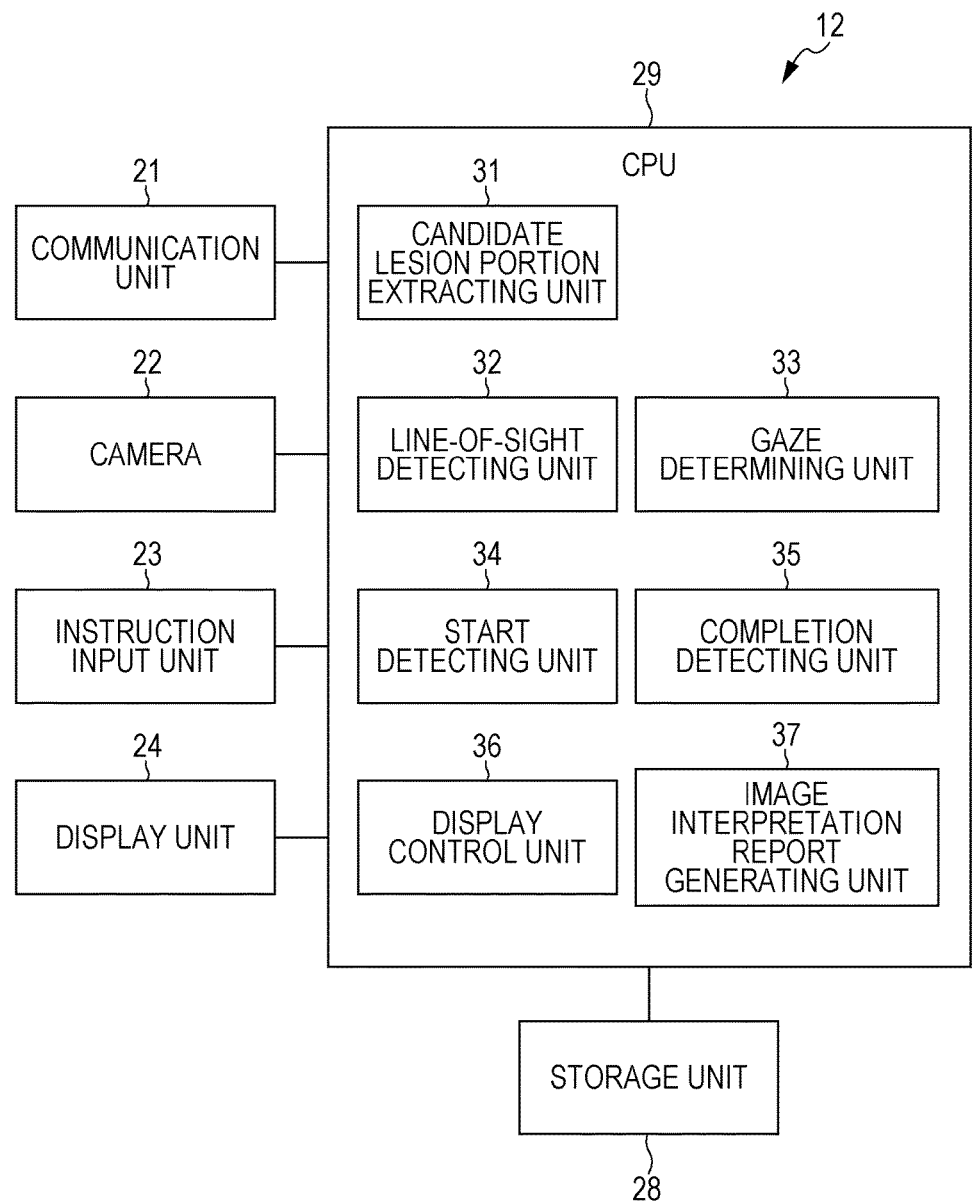
FIG. 2 is a block diagram illustrating a configuration example of an image interpretation support apparatus of a first embodiment.

FIG. 2 is a block diagram illustrating a configuration example of an image interpretation support apparatus 12 of a first embodiment according to the present invention.

The image interpretation support apparatus 12 of this embodiment includes a communication unit 21 capable of communicating with each device (for example, the database 16) connected to the local area network 18, a camera 22 that captures and outputs an image of a person who reads an image (hereinafter referred to as a person image), an instruction input unit 23 that receives input of an instruction from the person who reads an image, a display unit 24 that displays information for the person who reads an image, a storage unit 28 that stores a program to support image interpretation and information needed to execute the program, and a CPU (central processing unit) 29 that controls each unit in the image interpretation support apparatus 12 in accordance with the program stored in the storage unit 28.

The CPU 29 of this embodiment includes a candidate lesion portion extracting unit 31 that analyzes a medical image to be interpreted, which is obtained from the database 16 through the communication unit 21, and extracts a candidate lesion portion from the medical image to be interpreted; a line-of-sight detecting unit 32 that calculates a position at which a line of sight of the person who reads an image is directed (hereinafter referred to as a line-of-sight position) in the medical image to be interpreted that is displayed on the display unit 24 by detecting the line of sight of the person who reads an image by using an image of the person who reads an image captured by the camera 22; a gaze determining unit 33 that determines, in accordance with a detection result obtained by the line-of-sight detecting unit 32, whether the candidate lesion portion in the medical image to be interpreted that is displayed on the display unit 24 has been gazed at by the person who reads an image; a start detecting unit 34 that detects start of image interpretation, by the person who reads an image, of the medical image to be interpreted that is displayed on the display unit 24; a completion detecting unit 35 that detects completion of image interpretation, by the person who reads an image, of the medical image to be interpreted that is displayed on the display unit 24; a display control unit 36 that performs display control of the display unit 24 in accordance with an extraction result obtained by the candidate lesion portion extracting unit 31, a detection result obtained by the line-of-sight detecting unit 32, a determination result obtained by the gaze determining unit 33, a detection result obtained by the start detecting unit 34, and a detection result obtained by the completion detecting unit 35; and an image interpretation report generating unit 37 that generates an image interpretation report in accordance with the image interpretation result or the like that is provided by the person who reads an image, which is input through the instruction input unit 23.

The display unit 24 is capable of displaying the medical image to be interpreted and a support image indicating a candidate lesion portion as needed in accordance with the display control performed by the display control unit 36.

Next, specific examples of support information extracted by the candidate lesion portion extracting unit 31 will be described.

Figure 3:
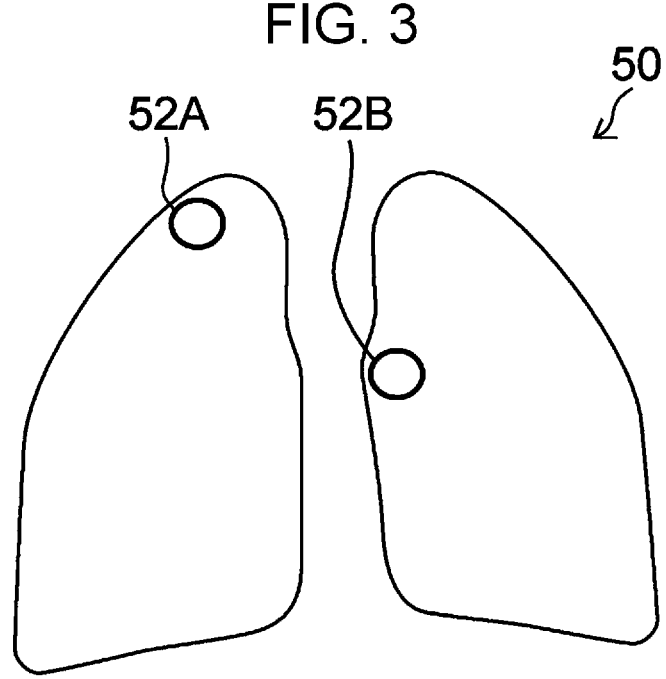
FIG. 3 is an explanatory illustration used to describe an example of support information.

FIG. 3 illustrates marks 52A and 52B that are closed curves enclosing the entirety of or a part of each candidate lesion portion. Marks 52A and 52B are superimposed on a medical image 50 displayed on the display unit 24 to represent signs to indicate candidate lesion portions. In this example, marks 52A and 52B, which are closed curves, are support information. As a closed curve, for example, an enclosing line (for example, a circle or a polygon) that circumscribes the candidate lesion portion is used.

Figure 4:
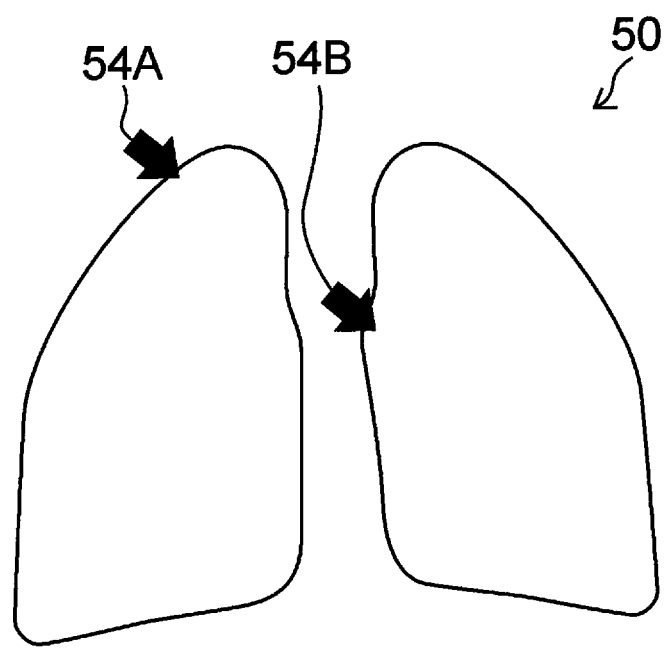
FIG. 4 is an explanatory illustration used to describe another example of support information.

FIG. 4 illustrates marks 54A and 54B that are arrows pointing at each candidate lesion portion. Marks 54A and 54B are superimposed on the medical image 50 displayed on the display unit 24 to represent signs to indicate candidate lesion portions. In this example, marks 54A and 54B, which are arrows, are support information.

Although the examples in which two candidate lesion portions are present in the medical image 50 are illustrated in FIGS. 3 and 4, the number of the candidate lesion portions in the medical image 50 changes depending on a state of a subject. The number of the marks, which are an example of support information added to the medical image 50, is not limited to two and may be one, more than or equal to three, or even zero.

The support information in the present invention is not particularly limited to the marks (for example, 52A and 54A) illustrated in FIGS. 3 and 4. Any information capable of supporting image interpretation by the person who reads an image can be used. The support information is not limited to figures and may be represented by colors, patterns, or the like. The support information may be represented only by text or by a combination of a figure and text. Further, the support information is not limited to visual information, and aural information (for example, voice data) or tactile information (for example, vibration) may be output along with the visual information.

The support information extracted from the medical image by the candidate lesion portion extracting unit 31 is not only stored in the storage unit 28, but also registered in the database 16 through the communication unit 21 in this example. In other words, the support information can be used not only by the image interpretation support apparatus 12, which has extracted the support information, but also by other image interpretation support apparatuses 12 or other kinds of apparatuses that are connected to the local area network 18 by accessing the database 16.

Next, a specific example of line-of-sight detection by the line-of-sight detecting unit 32 will be described.

The line-of-sight detecting unit 32 in this example extracts a fixed part and a moving part of an eye of the person who reads an image from a person image captured by the camera 22 and detects the position of the moving part of the eye with respect to the fixed part of the eye. Then, the line-of-sight detecting unit 32 calculates the line-of-sight position on the medical image in accordance with the position of the moving part of the eye thus detected. A movement path of the line-of-sight position may be detected by the line-of-sight detecting unit 32.

Referring to FIG. 5, a description will be given of an example of detecting the line of sight by detecting the movement of the iris of an eye by using an imaging device sensitive to visible light serving as the camera 22. The line-of-sight detecting unit 32 extracts, as a reference point, at least one of an inner corner 62 of an eye or an outer corner 64 of the eye from a person image 60 and calculates the reference point coordinates. The line-of-sight detecting unit 32 also extracts an iris part 66 as a moving point from the person image 60 and calculates the moving point coordinates. Then, the line-of-sight detecting unit 32 derives the line-of-sight position of the person who reads an image by using the positional relationship of the moving point coordinates with respect to the reference point coordinates.

An imaging device that captures an image by emitting infrared light may be used as the camera 22, and the line of sight may be detected by using the positional relationship between corneal reflection and a pupil of the person who reads an image. The line-of-sight detecting unit 32 extracts the corneal reflection from the person image 60 as a reference point and calculates the reference point coordinates. The line-of-sight detecting unit 32 also extracts the pupil part (68 in FIG. 5) as the moving point from the person image 60 and calculates the moving point coordinates. Then, the line-of-sight detecting unit 32 derives the line-of-sight position of the person who reads an image by using the positional relationship of the moving point coordinates with respect to the reference point coordinates. Although the line-of-sight detection using infrared light needs a device that can capture an image by emitting infrared light, detection accuracy of a line-of-sight position is usually easy to improve.

The line-of-sight detection in the present invention is not particularly limited to the cases described with reference to FIG. 5. Other known techniques that can detect the line of sight of the person who reads an image may be used for the line-of-sight detection. However, it is necessary to use line-of-sight detection techniques whose accuracy of positioning a line of sight is ensured to the extent that whether the line of sight is directed at a candidate lesion portion in the medical image can be determined.

Next, gaze determination performed by the gaze determining unit 33 will be described in detail.

In a case where the line of sight of the person who reads an image is directed at a candidate lesion portion in the medical image to be interpreted that is displayed on the display unit 24, the gaze determining unit 33 in this example determines whether the person who reads an image is in a gazing state in which the person who reads an image is gazing at the candidate lesion portion or in a non-gazing state in which the person who reads an image is not gazing at the candidate lesion portion while the line of sight of the person who reads an image is directed at the candidate lesion portion. There are various ways to determine such gazing states.

For example, there is a method to determine whether the person who reads an image is in the gazing state or in the non-gazing state by using the time during which the line of sight of the person who reads an image dwells on a candidate lesion portion. In a case where the line-of-sight position is in a region of a candidate lesion portion in the medical image displayed on the display unit 24, the gaze determining unit 33 measures the time (a dwell time) during which the line-of-sight position continuously dwells in the region of the candidate lesion portion and determines that the person who reads an image is in the gazing state in a case where the dwell time exceeds a threshold value (a predetermined duration). If the line-of-sight position moves and remains in the region of the same candidate lesion portion, the dwell time is accumulated because the line-of-sight position is considered to "continuously dwell". If the line-of-sight position moves to a region of another candidate lesion portion in the predetermined duration, the gaze determining unit 33 determines that the person who reads an image is in the non-gazing state, and the dwell time returns to zero.

For another example, there is a method to determine whether the person who reads an image is in the gazing state or in the non-gazing state in accordance with a condition of the pupil of the person who reads an image. For example, the gaze determining unit 33 extracts the pupil part from the person image, detects at least one of a positional change of the pupil part, a change in the pupil shape, or a change in the pupil size, and performs determination in accordance with the change thus detected. In this example, the line-of-sight detecting unit 32 not only derives the line-of-sight position, but also detects the condition of the pupil of the person who reads an image.

Next, a specific example of the start detecting unit 34 and the completion detecting unit 35 will be described.

The start detecting unit 34 and the completion detecting unit 35 in this example respectively receive an operation to start image interpretation and an operation to complete image interpretation from the person who reads an image through the instruction input unit 23 and respectively detect start and completion of the image interpretation. For example, the start detecting unit 34 and the completion detecting unit 35 respectively receive input of an instruction to start image interpretation and an instruction to complete image interpretation from the person who reads an image through a manual input device, such as a keyboard, a mouse, or a touch sensor. The start detecting unit 34 and the completion detecting unit 35 may respectively receive input of an instruction to start image interpretation and an instruction to complete image interpretation through a device using non-manual input, such as voice input or gesturing input.

Input of the instruction to start image interpretation and the instruction to complete image interpretation from the person who reads an image may be received in accordance with the line-of-sight detection performed by the line-of-sight detecting unit 32. Instructions that may be input in accordance with the line-of-sight detection are not limited to the instruction to start image interpretation and the instruction to complete image interpretation, and other instructions may be input in accordance with the line-of-sight detection.

Next, the display control performed by the display control unit 36 will be described in detail.

In a case where the start detecting unit 34 detects the start of the image interpretation by the person who reads an image, the display control unit 36 in this example sets the display unit 24 to a first display state (a state in which the medical image to be interpreted is displayed and the support information is not displayed). In addition, in a case where the completion detecting unit 35 detects the completion of the image interpretation by the person who reads an image and the gaze determining unit 33 determines that a candidate lesion portion has been gazed at after the start of the image interpretation, the display control unit 36 keeps the display unit 24 in the first display state. On the other hand, in a case where the completion detecting unit 35 detects the completion of the image interpretation by the person who reads an image and the gaze determining unit 33 determines that the candidate lesion portion has not been gazed at after the start of the image interpretation, the display control unit 36 switches the display unit 24 from the first display state to a second display state (a state in which at least the support information is displayed).

Figure 6B:
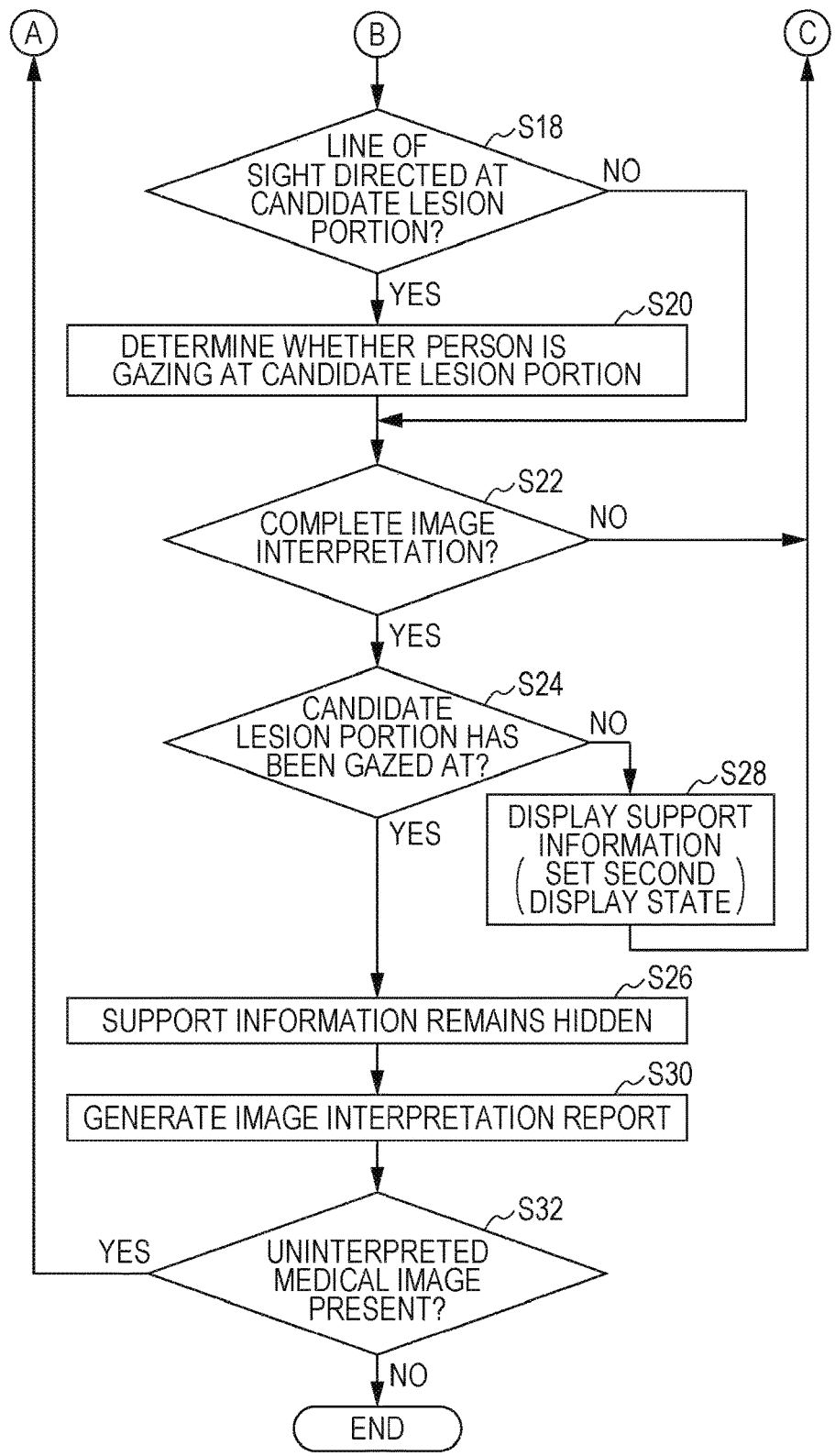

FIGS. 6A and 6B depict a flowchart illustrating a process flow of an example of an image interpretation support method using the image interpretation support apparatus of the first embodiment. The process is executed by the CPU 29 in accordance with a program stored in advance in the storage unit 28.

First, a medical image to be interpreted is obtained from the database 16 through the communication unit 21 (step S2).

Next, the candidate lesion portion extracting unit 31 analyzes the medical image to be interpreted and extracts a candidate lesion portion from the medical image to be interpreted (step S4). The candidate lesion portion extracting unit 31 generates support information indicating the candidate lesion portion. For example, marks 52A and 52B (support information) depicted in FIG. 3 or marks 54A and 54B (support information) depicted in FIG. 4 are generated in accordance with the analysis result of the medical image. In this example, the phrase "extract a candidate lesion portion" means to identify, by image processing, an image of a portion that is present in the medical image and is a possible lesion portion (a candidate lesion portion) and generate at least the information indicating the position of the candidate lesion portion in the medical image as support information. In a case where marks 52A and 52B, which are closed curves depicted in FIG. 3, are generated as the support information, not only a representative position (for example, the center position) of a candidate lesion portion, but also an outline of a region of the candidate lesion portion (or information defining a figure that circumscribes the candidate lesion portion), or the size of the candidate lesion portion is identified by image processing, and the support information is generated.

Next, it is determined whether the person who reads the image starts image interpretation of the medical image to be interpreted in accordance with the detection result obtained by the start detecting unit 34 (step S12). In this example, input of an instruction to start image interpretation from the person who reads the image is received through the instruction input unit 23. In other words, the intention of the person who reads the image to start image interpretation is detected.

If it is determined to start image interpretation (YES in step S12), the display control unit 36 causes the display unit 24 to display the medical image to be interpreted and not to display support information (step S14). In other words, the display control unit 36 sets the display unit 24 to the first display state.

Next, the line-of-sight detecting unit 32 detects a line of sight of the person who reads the image (step S16).

Then, it is determined whether the line of sight of the person who reads the image is directed at the candidate lesion portion in the medical image to be interpreted that is displayed on the display unit 24 in accordance with the detection result obtained by the line-of-sight detecting unit 32 (step S18). If it is determined that the line of sight of the person who reads the image is directed at the candidate lesion portion (YES in step S18), the gaze determining unit 33 determines whether the person who reads the image is in the gazing state, in which the person who reads the image is gazing at the candidate lesion portion, or in the non-gazing state, in which the person who reads the image is not gazing at the candidate lesion portion while the line of sight of the person who reads the image is directed at the candidate lesion portion (step S20).

Next, it is determined whether the image interpretation of the medical image to be interpreted is completed in accordance with the detection result obtained by the completion detecting unit 35 (step S22). In this example, input of an instruction to complete image interpretation from the person who reads the image is received through the instruction input unit 23. In other words, the intention of the person who reads the image to complete image interpretation is detected.

If it is determined that the image interpretation is not completed (NO in step S22), steps S16 to S22 are repeated.

If it is determined that the image interpretation is completed (YES in step S22), it is determined whether the candidate lesion portion has been gazed at after the start of the image interpretation (step S24).

In a case where the completion detecting unit 35 detects the completion of the image interpretation and the gaze determining unit 33 determines that the candidate lesion portion has been gazed at after the start of the image interpretation (YES in step S24), the support information remains hidden on the display unit 24 (step S26). In other words, the display control unit 36 keeps the display unit 24 in the first display state. In a case where the completion detecting unit 35 detects the completion of the image interpretation and the gaze determining unit 33 determines that the candidate lesion portion has been gazed at (YES in step S24), the display control unit 36 may switch the display unit 24 to a display state in which the support information is not displayed and that is different from the first display state.

In a case where the completion detecting unit 35 detects the completion of the image interpretation and the gaze determining unit 33 determines that the candidate lesion portion has not been gazed at after the start of the image interpretation (NO in step S24), the support information is displayed on the display unit 24 (step S28). In other words, the display control unit 36 switches the display unit 24 from the first display state to the second display state.

For example, in the case where marks 52A and 52B depicted in FIG. 3 are generated as the support information, as depicted in FIG. 7, marks 52A and 52B are not displayed in the first display state and displayed in the second display state. In FIG. 7, a message "Not gazed!" is displayed along with marks 52A and 52B on the display unit 24.

After the second display state is set, the process returns to S16, so that the image interpretation by the person who reads the image resumes. Although the image interpretation resumes in the second display state in this example, the display unit 24 may be returned to the first display state in response to an instruction that is input by the person who reads the image or when a fixed period of time elapses.

In a case where the completion detecting unit 35 detects the completion of the image interpretation and the gaze determining unit 33 determines that the candidate lesion portion has been gazed at after the start of the image interpretation (YES in step S24), while the support information remains hidden on the display unit 24 (step S26), an image interpretation report is generated in response to input of an image interpretation result provided by the person who reads the image through the instruction input unit 23 (step S30). The generated image interpretation report is transmitted to the database 16 through the communication unit 21 and stored in the database 16.

Next, it is determined whether an uninterpreted medical image is present among medical images to be interpreted in the database 16 (step S32). If it is determined that an uninterpreted medical image is present (YES in step S32), the process returns to step S12 so that the person who reads the image can interpret the next medical image. If it is determined that no uninterpreted medical image is present (NO in step S32), the process is completed.

Variations in Display Control

To facilitate an understanding of the present invention, referring to FIG. 7, a description has been given of an example in which all the support information is displayed in the case where a candidate lesion portion that has not been gazed at is present in a case where the person who reads the image intends to complete the image interpretation (NO in step S24 in FIG. 6B). The present invention is not limited to this case.

Figure 8:
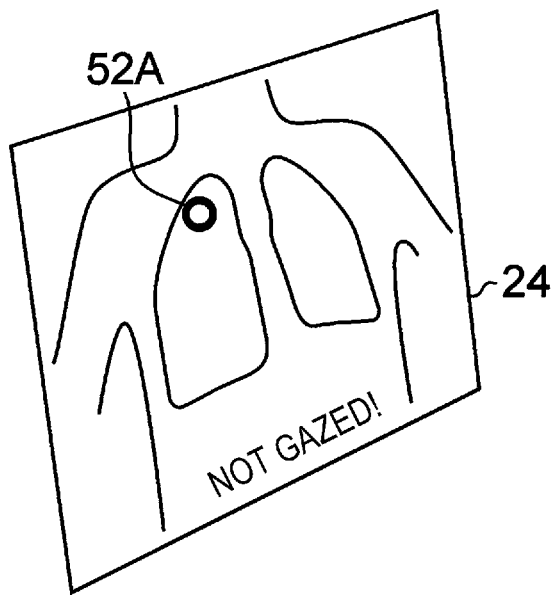
FIG. 8 is an explanatory illustration used to describe a case where support information of a candidate lesion portion that has been gazed at is not displayed.

Preferably, display control is performed to enable the person who reads the image to easily identify only a candidate lesion portion that has not been gazed at among a plurality of candidate lesion portions. As depicted in FIG. 3, in a case where a plurality of candidate lesion portions are present in the medical image to be interpreted 50 and the plurality of marks 52A and 52B are generated as support information, the display control unit 36 causes the display unit 24 not to display the mark indicating a candidate lesion portion that the person who reads the image has gazed at (for example, 52B) among the plurality of candidate lesion portions and causes the display unit 24 to display only the mark indicating a candidate lesion portion that the person who reads the image has not gazed at (for example, mark 52A) in the second display state, as depicted in FIG. 8.

Figure 9:
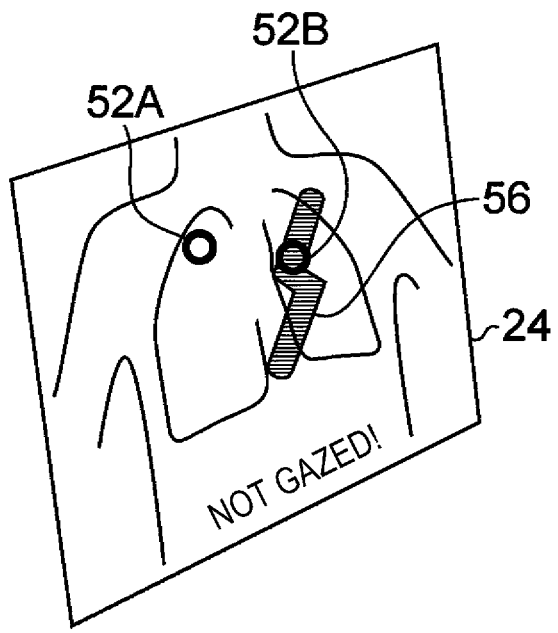
FIG. 9 is an explanatory illustration used to describe a case where a display mode of a region that has been gazed at is changed.

In addition, it is preferable to enable the person who reads the image to intuitively grasp the relationship among a movement of the line of sight, a region that has been gazed at, and a region that has not been gazed at by performing display control that interactively responds to a sequential movement of the line of sight of the person who reads the image. As depicted in FIG. 3, in a case where a plurality of candidate lesion portions are present in the medical image 50 to be interpreted and the plurality of marks 52A and 52B are generated as the support information, the display control unit 36 changes a display mode of the candidate lesion portion that the person who reads the image has gazed at among the plurality of candidate lesion portions in accordance with the sequential movement of the line of sight of the person who reads the image. For example, as depicted in FIG. 9, the display control unit 36 sequentially changes the color or pattern of a region 56 that has been gazed at and that includes the candidate lesion portion that has been gazed at in the medical image to be interpreted, in accordance with the sequential movement of the line of sight of the person who reads the image. For example, the display control unit 36 performs interactive display control so as to imitate an eraser gradually erasing the region 56 that has been gazed at as the line of sight moves. If it becomes more difficult, rather than easier, to identify the lesion portion by completely erasing the region that has been gazed at, the display control unit 36 preferably performs such display control as decreases the brightness of the region 56 that has been gazed at or produces a halftone image of the region 56 that has been gazed at.

In other words, when a candidate lesion portion that has not been gazed at changes to a candidate lesion portion that has been gazed at, the display control unit 36 changes the display mode of the candidate lesion portion that has been gazed at so that the person who reads the image can discriminate between the candidate lesion portion that has not been gazed at and the candidate lesion portion that has been gazed at. The phrase "change the display mode of the candidate lesion portion that has been gazed at" is meant to include the case where the display control unit 36 changes the display mode of the region 56 that has been gazed at and that includes the candidate lesion portion that has been gazed at in the medical image to be interpreted, as described with reference to FIG. 9.

In addition, the display control unit 36 may perform control to display an enlarged image of the region at which the line of sight is directed in the medical image to be interpreted. In other words, the display control unit 36 performs control to display an enlarged image of only the region corresponding to the line-of-sight position (for example, the region within a circle that is centered around the line-of-sight position and has a fixed radius) in the medical image to be interpreted in accordance with the line-of-sight detection result obtained by the line-of-sight detecting unit 32. In addition, the display control unit 36 stops performing control to display an enlarged image of a region distant from the line-of-sight position (for example, a region outside the circle that is centered around the line-of-sight position and has the fixed radius) in the medical image to be interpreted. The display control unit 36 may stop performing control to display the enlarged image of the region distant from the line-of-sight position when a fixed period of time has elapsed from when the display control unit 36 starts performing control to display the enlarged image of the region.

The display control unit 36 may also perform display control to decrease the visibility of a portion that does not need to be gazed at in the medical image to be interpreted compared with the visibility of a candidate lesion portion. For example, a portion excluding a candidate lesion portion in the medical image (a portion other than a candidate lesion portion) is subjected to display control such as decreasing the brightness of the portion or producing a halftone image of the portion, performed by the display control unit 36. Not only the visibility of a candidate lesion portion, but also the visibility of a portion surrounding a candidate lesion portion (for example, a portion within a fixed distance from a candidate lesion portion) may be increased, and the visibility of only a region distant from a candidate lesion portion may be relatively decreased.

Second Embodiment

FIG. 10 is a block diagram illustrating a configuration example of an image interpretation support apparatus 12 of a second embodiment according to the present invention. Elements that are the same as those of the image interpretation support apparatus 12 of the first embodiment depicted in FIG. 2 are denoted by the same numerals, and descriptions that have already been given will be omitted hereinafter.

In FIG. 10, a fatigue deducing unit 41 deduces whether the person who reads an image needs recovery from fatigue caused by image interpretation. A warning unit 42 outputs a warning to the person who reads an image in a case where the fatigue deducing unit 41 deduces that the recovery from fatigue is needed for the person who reads an image.

There are various ways for the fatigue deducing unit 41 to deduce fatigue. The fatigue deducing unit 41 of this example deduces whether recovery from fatigue is needed by using the number of switching operations from the first display state (a state in which the support information is not displayed) to the second display state (a state in which the support information is displayed), performed by the display control unit 36. Other ways for fatigue deduction will be described below.

A warning may be output by the warning unit 42 by using the display unit 24 or a speaker 25. A warning output by the speaker 25 may be a voice output or an alarm output. In addition, a warning is not limited to a visual output or an aural output and may be a tactile output (for example, vibration generation).

Figure 11B:
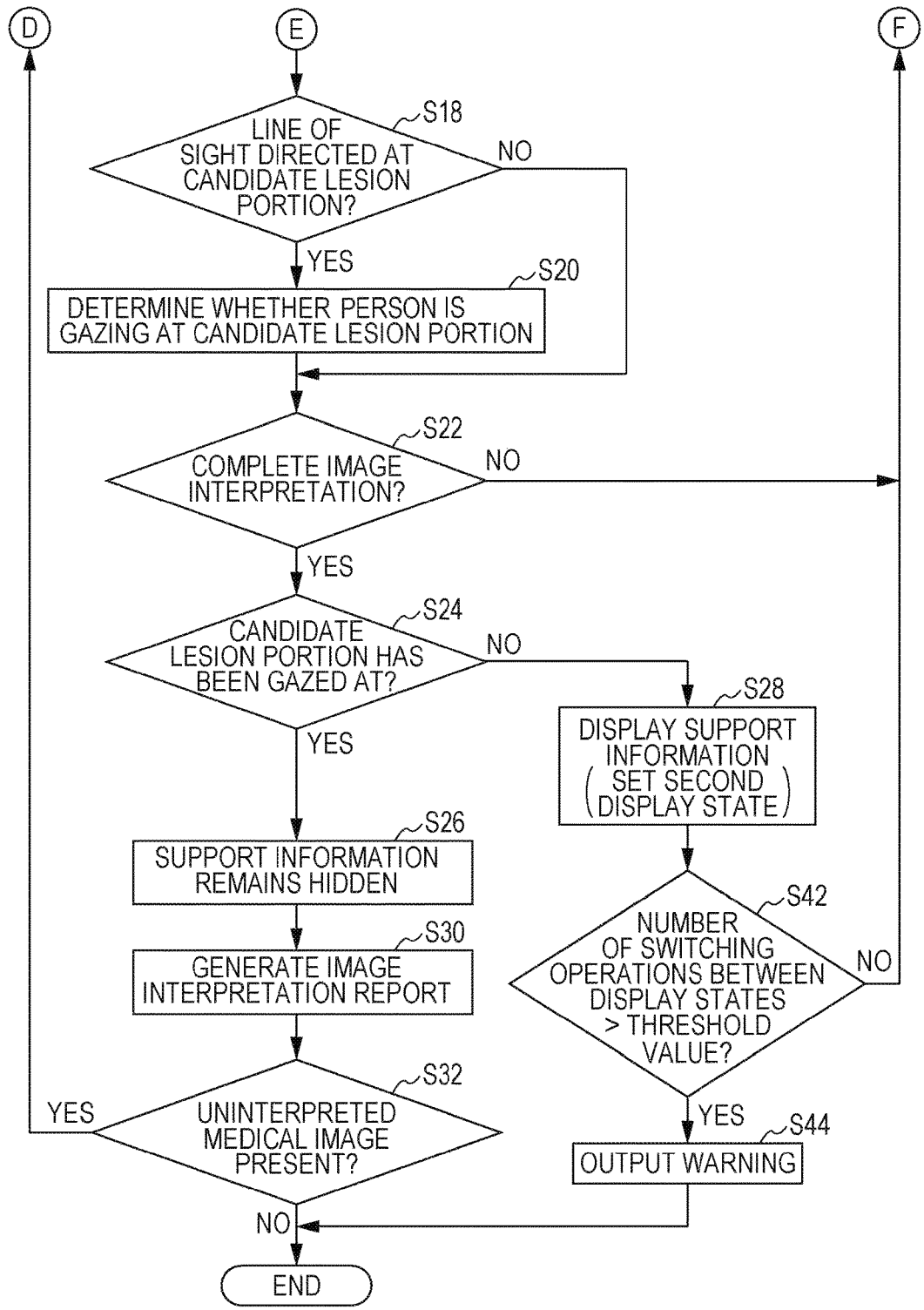

FIGS. 11A and 11B depict a flowchart illustrating a process flow of an example of an image interpretation support method using the image interpretation support apparatus 12 of the second embodiment. This process is executed by the CPU 29 in accordance with a program stored in advance in the storage unit 28. Steps that are the same as those in the process in the first embodiment depicted in FIGS. 6A and 6B are denoted by the same numerals, and only different items will be described below.

In this embodiment, in a case where the completion detecting unit 35 detects the completion of the image interpretation and the gaze determining unit 33 determines that the candidate lesion portion has not been gazed at after the start of the image interpretation (NO in step S24), the display control unit 36 performs control to switch from the first display state (in which the support information is not displayed) to the second display state (in which the support information is displayed) (step S28). Subsequently, the number of switching operations from the first display state to the second display state is compared with a threshold value (step S42). Although the comparison may be made between the number of switching operations counted for a single medical image to be interpreted and a threshold value, it is preferable to count the number of switching operations for a plurality of medical images (each of the plurality of medical images corresponding to one of a plurality of subjects) that the person who reads images has interpreted continuously and compare the count with a threshold value. A configuration in which the total number of switching operations per fixed number of images is compared with a threshold value may be employed, or a configuration in which the total number of switching operations for a variable number of images is compared with a threshold value may be employed.

If the number of switching operations from the first display state to the second display state is less than or equal to the threshold (NO in step S42), the process returns to step S16, and image interpretation is resumed.

If the number of switching operations from the first display state to the second display state exceeds the threshold (YES in step S42), a warning is output by using at least one of the display unit 24 or the speaker 25 under the control of the warning unit 42 (step S44) in this example.

In this example, if a warning is output, the process is halted, and the image interpretation is interrupted. After the warning is output, the image interpretation may be resumed based on a decision by the person who reads the image. In short, the process returns to step S12 in FIG. 11A.

Variations in Fatigue Deduction

With reference to FIGS. 11A and 11B, a description has been given of a mode in which it is determined whether a warning is to be output (i.e., deducing whether the person who reads an image needs recovery from fatigue) in accordance with the number of switching operations from the first display state to the second display state (i.e., the number of instances where it is determined that a candidate lesion portion that has not been gazed at is present although the person who reads an image intends to complete the image interpretation). The present invention is not limited to such a case. For example, configurations in which the following variations 1 to 3 are performed may be employed.

Variation 1 in Fatigue Deduction

Fatigue of the person who reads an image is deduced by using an accumulated duration of image interpretation by the person who reads an image. For example, by using an internal timer of the CPU 29 (a timer disposed peripherally to the CPU 29 may also be used), the fatigue deducing unit 41 calculates an accumulated duration from the start of image interpretation to the completion of image interpretation and compares the accumulated duration with a threshold value. Preferably, as the accumulated duration, an accumulated duration of image interpretation in which the person who reads an image has continuously interpreted a plurality of medical images is used. For example, an accumulated duration of image interpretation in which a variable number of images have been continuously interpreted is compared with the threshold value.

Variation 2 in Fatigue Deduction

Fatigue of the person who reads an image is deduced by using at least one of a moving speed or an amount of movement of the line of sight of the person who reads an image. For example, the fatigue deducing unit 41 calculates and compares at least one of the moving speed or the amount of movement of the line of sight of the person who reads an image with a threshold value by using the line-of-sight detection result obtained by the line-of-sight detecting unit 32. The terms "moving speed" and "amount of movement" may denote calculated values for the medical image at which the line of sight is currently directed or average values of calculated values for a plurality of medical images that the person who reads an image has continuously interpreted. For example, an average value (a moving average) of moving speeds of the line of sight that is calculated for a fixed number of images that have been interpreted continuously is compared with a threshold value.

Variation 3 in Fatigue Deduction

Fatigue of the person who reads an image is deduced by using a blink speed of the person who reads an image. For example, as illustrated in FIG. 12, a blink detecting unit 38 is added and the blink detecting unit 38 detects a blink of eyes of the person who reads an image by using a person image captured by the camera 22. The fatigue deducing unit 41 calculates and compares a speed of the blink of the eyes of the person who reads an image with a threshold value. Then, in a case where the speed of the blink of the eyes is below the threshold value, the fatigue deducing unit 41 deduces that the person who reads an image needs recovery from fatigue. In this mode, a human characteristic in which the speed of the blink becomes slower when tired, compared with when not tired, is used. For example, fatigue is deduced by calculating a blink duration from a time during which the line of sight is not directed at any portion of the medical image and comparing the blink duration with a threshold value. In this case, the blink detecting unit 38 detects a blink by using an output of the line-of-sight detecting unit 32.

A variation for deducing fatigue in the present invention is not particularly limited to the variations 1 to 3 described above. The accuracy of deducing fatigue may be improved by combining various variations.

Third Embodiment

Figure 13:
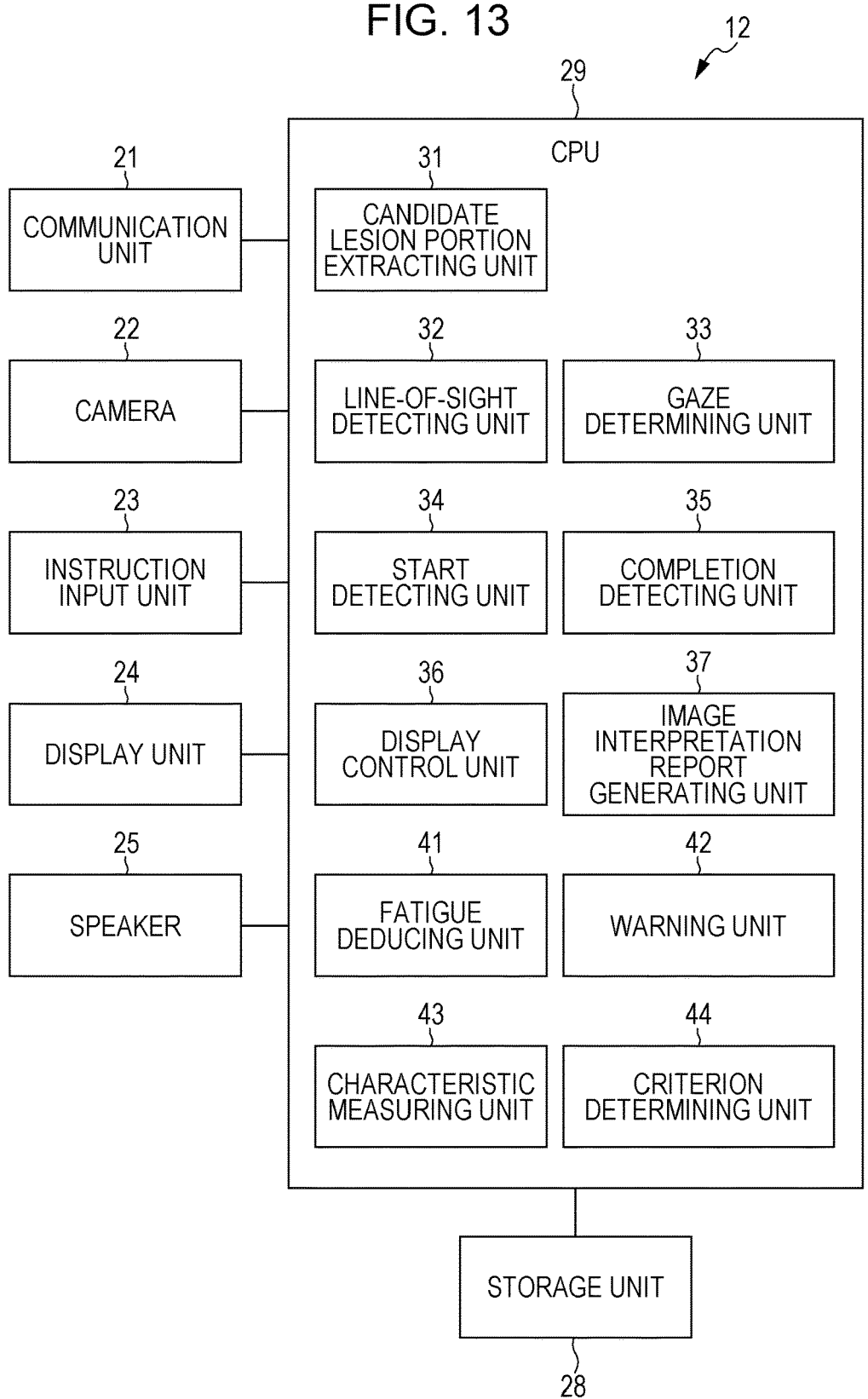
FIG. 13 is a block diagram illustrating a configuration example of an image interpretation support apparatus of the third embodiment.

FIG. 13 is a block diagram illustrating a configuration example of an image interpretation support apparatus 12 of a third embodiment according to the present invention. Elements that are the same as those of the image interpretation support apparatus 12 of the second embodiment depicted in FIG. 10 are denoted by the same numerals, and descriptions that have already been given will be omitted hereinafter.

Referring to FIG. 13, a characteristic measuring unit 43 measures gaze characteristic of the person who reads an image for each individual. A criterion determining unit 44 determines a criterion for determining whether the person who reads an image is in a gazing state or in a non-gazing state and a criterion for deducing whether the person who reads an image needs recovery from fatigue by using a measurement result for each individual (individual data of each person who reads an image) obtained by the characteristic measuring unit 43. The gaze determining unit 33 in this embodiment determines whether the person who reads an image is in a gazing state or in a non-gazing state in accordance with the criterion determined for each individual by the criterion determining unit 44. In addition, the fatigue deducing unit 41 in this embodiment deduces whether the person who reads an image needs recovery from fatigue in accordance with the criterion determined for each individual by the criterion determining unit 44.

For example, when execution of an image interpretation support program is started, the characteristic measuring unit 43 displays a test pattern to measure a characteristic of each individual on an initial screen of the display unit 24, moves the test pattern on the screen, and measures the tracking ability of the line of sight of the person who reads an image to a movement of a test pattern. The criterion determining unit 44 determines a criterion for determining whether the person who reads an image is in a gazing state or in a non-gazing state by using the tracking ability of the line of sight of the person who reads an image measured by the characteristic measuring unit 43. The criterion determining unit 44 also determines a criterion for deducing whether recovery from fatigue is necessary by using the tracking ability of the line of sight of the person who reads an image measured by the characteristic measuring unit 43.

The mode used by the characteristic measuring unit 43 to measure the characteristic is not particularly limited to the case as described above, which uses a test pattern. Instead of displaying a test pattern, measuring the characteristic may be performed by using at least one of a line-of-sight movement or a change in an eye condition of the person who reads an image during image interpretation.

There are a variety of targets for which a criterion is to be determined by the criterion determining unit 44. The phrase "a criterion determined for each individual" by the criterion determining unit 44 also means a case where a predetermined criterion is automatically adjusted for each person who reads an image.

Fourth Embodiment

Figure 14:
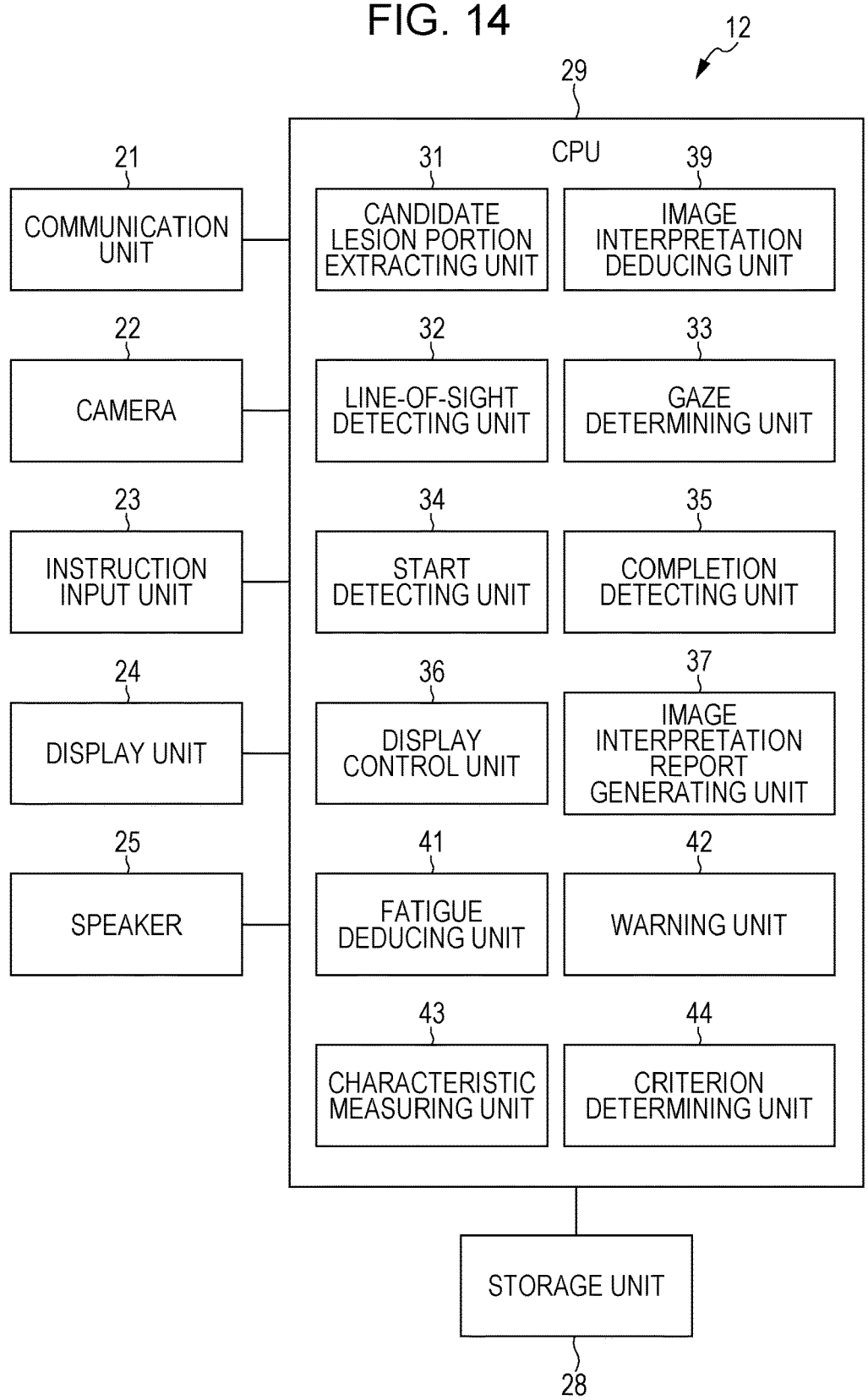
FIG. 14 is a block diagram illustrating a configuration example of an image interpretation support apparatus of a fourth embodiment.

FIG. 14 is a block diagram illustrating a configuration example of an image interpretation support apparatus 12 of a fourth embodiment according to the present invention. Elements that are the same as those of the image interpretation support apparatus 12 of the third embodiment depicted in FIG. 13 are denoted by the same numerals, and descriptions that have already been given will be omitted hereinafter.

Referring to FIG. 14, an image interpretation deducing unit 39 deduces whether the person who reads an image has performed image interpretation in accordance with an enlarging operation performed on the medical image to be interpreted. The completion detecting unit 35 detects completion of image interpretation only in a case where the image interpretation deducing unit 39 deduces that image interpretation has been performed. In other words, even if the person who reads an image intends to complete interpreting an image, the case where it is deduced that image interpretation has not actually been performed is excluded, and thereby, the detection accuracy of the completion of the image interpretation can be improved.

Variation in System Configuration

Obviously, an image interpretation support apparatus 12 according to the present invention may be constituted by a plurality of devices, and processes that are necessary to support image interpretation may be split and performed by the plurality of devices. In other words, the image interpretation support apparatus 12 depicted in FIG. 1 may be constituted by a plurality of devices.

Figure 15:
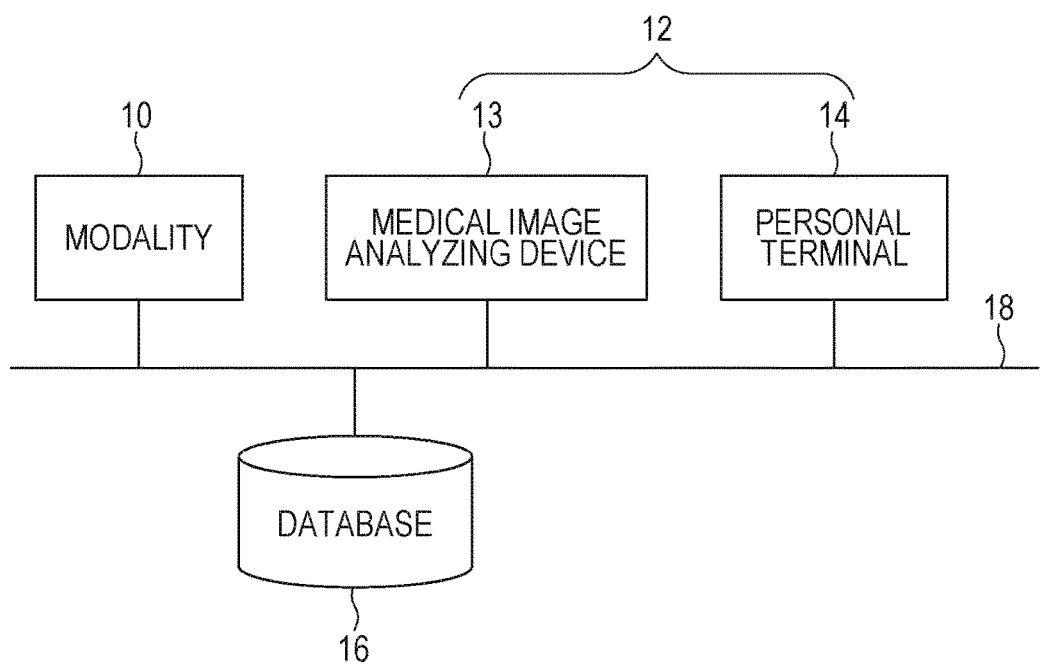
FIG. 15 is a system configuration diagram illustrating another example of a medical system including the image interpretation support apparatus according to an aspect of the present invention.

FIG. 15 illustrates a system configuration example of the image interpretation support apparatus 12 depicted in FIG. 1, constituted by a medical image analyzing device 13 and a personal terminal 14.

In FIG. 15, the medical image analyzing device 13 includes the candidate lesion portion extracting unit 31 (the unit denoted as 31 in FIG. 2, 10, 12, 13, or 14). The personal terminal 14 is a terminal operated by the person who reads an image. The personal terminal 14 may be a device constituted by the image interpretation support apparatus 12 described in the first embodiment to the fourth embodiment with the candidate lesion portion extracting unit 31 removed. A communication unit 21 of the personal terminal 14 obtains, from the database 16 through communication via the local area network 18, a medical image to be interpreted and support information that indicates a candidate lesion portion extracted from the medical image.

Obviously, the present invention is not limited to the embodiments described above, and various changes are possible within the gist of the present invention.

REFERENCE SIGNS LIST 10 modality
12 image interpretation support apparatus
13 medical image analyzing device 14 personal terminal
16 database
18 local area network
21 communication unit
22 camera
23 instruction input unit
24 display unit
25 speaker
28 storage unit
29 CPU
31 candidate lesion portion extracting unit
32 line-of-sight detecting unit
33 gaze determining unit
34 start detecting unit
35 completion detecting unit
36 display control unit
37 image interpretation report generating unit
38 blink detecting unit
39 image interpretation deducing unit
41 fatigue deducing unit
42 warning unit
43 characteristic measuring unit
44 criterion determining unit

What is claimed is:

1. An image interpretation support apparatus comprising:
a candidate lesion portion extracting unit that analyzes an image to be interpreted and extracts a candidate lesion portion from the image to be interpreted;
a display unit that is capable of displaying the image to be interpreted and support information indicating the candidate lesion portion;
a line-of-sight detecting unit that detects a line of sight of a person who reads the image;
a gaze determining unit that determines, in accordance with a detection result obtained by the line-of-sight detecting unit, whether the candidate lesion portion in the image to be interpreted that is displayed on the display unit has been gazed at by the person who reads the image;
a completion detecting unit that detects completion of image interpretation, by the person who reads the image, of the image to be interpreted that is displayed on the display unit;
a display control unit that, in a case where the completion detecting unit detects the completion of image interpretation and the gaze determining unit determines that the candidate lesion portion has not been gazed at, switches from a first display state in which the image to be interpreted is displayed on the display unit and the support information is not displayed to a second display state in which at least the support information is displayed on the display unit;
a fatigue deducing unit that deduces whether the person who reads the image needs recovery from fatigue caused by the image interpretation; and
a warning unit that outputs a warning in a case where the fatigue deducing unit deduces that the recovery from fatigue is needed,
wherein the fatigue deducing unit deduces whether the recovery from fatigue is needed by using number of switching operations from the first display state to the second display state, performed by the display control unit.

2. The image interpretation support apparatus according to claim 1, wherein the display control unit keeps the first display state in a case where the completion detecting unit detects the completion of image interpretation and the gaze determining unit determines that the candidate lesion portion has been gazed at.

3. The image interpretation support apparatus according to claim 1, wherein, in a case where a plurality of candidate lesion portions are present in the image to be interpreted, in the second display state, the display control unit performs control not to display support information for a candidate lesion portion that the person who reads the image has gazed at among the plurality of candidate lesion portions, and the display control unit performs control to display support information for a candidate lesion portion that the person who reads the image has not gazed at.

4. The image interpretation support apparatus according to claim 2, wherein, in a case where a plurality of candidate lesion portions are present in the image to be interpreted, in the second display state, the display control unit performs control not to display support information for a candidate lesion portion that the person who reads the image has gazed at among the plurality of candidate lesion portions, and the display control unit performs control to display support information for a candidate lesion portion that the person who reads the image has not gazed at.

5. The image interpretation support apparatus according to claim 1, wherein, in a case where a plurality of candidate lesion portions are present in the image to be interpreted, the display control unit performs control to display, in a changed display mode, a candidate lesion portion that the person who reads the image has gazed at among the plurality of candidate lesion portions so as to discriminate the candidate lesion portion that the person who reads the image has gazed at from a candidate lesion portion that the person who reads the image has not gazed at.

6. The image interpretation support apparatus according to claim 2, wherein, in a case where a plurality of candidate lesion portions are present in the image to be interpreted, the display control unit performs control to display, in a changed display mode, a candidate lesion portion that the person who reads the image has gazed at among the plurality of candidate lesion portions so as to discriminate the candidate lesion portion that the person who reads the image has gazed at from a candidate lesion portion that the person who reads the image has not gazed at.

7. The image interpretation support apparatus according to claim 1, wherein the fatigue deducing unit further deduces whether the recovery from fatigue is needed by using an accumulated duration of the image interpretation.

8. The image interpretation support apparatus according to claim 1, wherein the fatigue deducing unit further deduces whether the recovery from fatigue is needed by using at least one of a moving speed or an amount of movement of the line of sight that is detected by the line-of-sight detecting unit.

9. The image interpretation support apparatus according to claim 1, further comprising:
a blink detecting unit that detects a blink of eyes of the person who reads the image,
wherein the fatigue deducing unit further deduces whether the recovery from fatigue is needed by using a speed of the blink of the eyes.

10. The image interpretation support apparatus according to claim 1, wherein the fatigue deducing unit deduces whether the recovery from fatigue is needed in accordance with individual data of the person who reads the image.

11. The image interpretation support apparatus according to claim 1, wherein the display control unit performs control to display an enlarged image of a region at which the line of sight is directed in the image to be interpreted, and stops performing control to display the enlarged image of the region, in a case where the line of sight moves away from the region or when a fixed period of time has elapsed from when the display control unit starts performing control to display the enlarged image of the region.

12. The image interpretation support apparatus according to claim 1, wherein the display control unit decreases visibility of a portion that does not need to be gazed at in the image to be interpreted compared with visibility of the candidate lesion portion.

13. The image interpretation support apparatus according to claim 1, wherein input of an instruction from the person who reads the image is received in accordance with a line-of-sight detection performed by the line-of-sight detecting unit.

14. The image interpretation support apparatus according to claim 1, wherein, in a case where the line of sight of the person who reads the image is directed at a candidate lesion portion in the image to be interpreted that is displayed on the display unit, the gaze determining unit determines whether the person who reads the image is in a gazing state in which the person who reads the image is gazing at the candidate lesion portion or in a non-gazing state in which the person who reads the image is not gazing at the candidate lesion portion while the line of sight of the person who reads the image is directed at the candidate lesion portion.

15. The image interpretation support apparatus according to claim 14, wherein the gaze determining unit determines whether the person who reads the image is in the gazing state or in the non-gazing state by using a time during which the line of sight of the person who reads the image dwells on the candidate lesion portion.

16. The image interpretation support apparatus according to claim 14, wherein the gaze determining unit determines whether the person who reads the image is in the gazing state or in the non-gazing state in accordance with a condition of a pupil of the person who reads the image.

17. The image interpretation support apparatus according to claim 14, further comprising:
a characteristic measuring unit that measures gaze characteristic of the person who reads the image for each individual; and
a criterion determining unit that determines a criterion for determining whether the person who reads the image is in the gazing state or in the non-gazing state for each individual by using a measurement result for each individual obtained by the characteristic measuring unit,
wherein the gaze determining unit determines whether the person who reads the image is in the gazing state or in the non-gazing state in accordance with the criterion determined for each individual by the criterion determining unit.

18. The image interpretation support apparatus according to claim 17,
wherein the characteristic measuring unit displays a test pattern on the display unit, moves the test pattern on a screen of the display unit, and measures a tracking ability of the line of sight of the person who reads the image to the movement of the test pattern, and
wherein the criterion determining unit determines a criterion for determining whether the person who reads the image is in the gazing state or in the non-gazing state by using the tracking ability of the line of sight of the person who reads the image measured by the characteristic measuring unit.

19. The image interpretation support apparatus according to claim 1, further comprising:
an image interpretation deducing unit that deduces whether the person who reads the image has performed image interpretation in accordance with an enlarging operation performed on the image to be interpreted,
wherein the completion detecting unit detects completion of image interpretation only in a case where the image interpretation deducing unit deduces that image interpretation has been performed.

20. An image interpretation support method comprising:
a step of analyzing an image to be interpreted and extracting a candidate lesion portion from the image to be interpreted;
a step of setting a first display state in which the image to be interpreted is displayed on a display unit and support information that indicates the candidate lesion portion is not displayed;
a step of detecting a line of sight of a person who reads the image;
a step of determining whether the candidate lesion portion in the image to be interpreted that is displayed on the display unit has been gazed at by the person who reads the image in accordance with a result of detection of the line of sight;
a step of detecting completion of image interpretation, by the person who reads the image, of the image to be interpreted that is displayed on the display unit;
a step of switching from the first display state in which the image to be interpreted is displayed on the display unit and the support information is not displayed to a second display state in which at least the support information is displayed on the display unit in a case where the completion of image interpretation is detected and gazing at the candidate lesion portion is not determined;
a step of deducing whether the person who reads the image needs recovery from fatigue caused by the image interpretation; and
a step of outputting a warning in a case where need of the recovery from fatigue is deduced,
wherein in the step of deducing whether the person who reads the image needs recovery from fatigue caused by the image interpretation, the need of the recovery from fatigue is deduced by using number of switching operations from the first display state to the second display state.

* * * * *